United States Patent [19]
Berryhill

[11] 3,992,926
[45] Nov. 23, 1976

[54] PRESSURE MEASURING METHOD AND APPARATUS WITH DIGITAL READOUT

[75] Inventor: Robert C. Berryhill, Redding, Calif.
[73] Assignee: Ber-Tek, Inc., Redding, Calif.
[22] Filed: July 28, 1975
[21] Appl. No.: 599,925

[52] U.S. Cl. .................................................. 73/80
[51] Int. Cl.² .......................................... A61B 3/16
[58] Field of Search ............................... 73/80, 81

[56] References Cited
UNITED STATES PATENTS

| | | |
|---|---|---|
| 3,390,572 | 7/1968 | Murr .................................. 73/80 |
| 3,406,565 | 10/1968 | Murr .................................. 73/80 |
| 3,452,589 | 7/1969 | Hargens et al. .................... 73/80 |
| 3,677,074 | 7/1972 | Murr .................................. 73/80 |
| 3,724,263 | 4/1973 | Rose et al. ........................ 73/80 |

*Primary Examiner*—James J. Gill
*Assistant Examiner*—Anthony V. Ciarlante
*Attorney, Agent, or Firm*—Edward B. Gregg; Warren M. Becker

[57] ABSTRACT

A pressure-measuring apparatus and method is described for providing a digital readout of the intra-ocular pressure of an eye. The apparatus comprises a transducer for applanating the cornea of an eye and providing a variable output proportional to pressure as the transducer is applied to the cornea. Electronic means responsive to a change in the output of the transducer is coupled to the transducer for providing a digital readout of the pressure sensed by the transducer when there is a change in the slope of the output of the transducer and the change in the slope has a predetermined polarity and exceeds a predetermined rate. Means are also provided for simultaneously displaying at least four digital readouts of pressure corresponding to four successive pressure measurements. The multiple readouts permit an operator to use the lowest of the four readouts as an accurate measure of intra-ocular pressure when the measurements are taken from a given eye.

6 Claims, 6 Drawing Figures

PRESSURE MEASURING METHOD AND APPARATUS WITH DIGITAL READOUT

BACKGROUND OF THE INVENTION

The present invention relates to pressure-measuring apparatus in general and in particular to an apparatus and method for measuring the internal pressure of an enclosed member, such as the intra-ocular pressure of an eye.

The intra-ocular pressure of an eye is that pressure associated with the presence of a fluid in the eye called aqueous humour, which is known to completely fill the anterior and posterior chambers of an eye. It is also known that it flows through the chambers in fluid passageways. If, for any reason, such as the presence of a condition known as glaucoma, the fluid flow of the aqueous humour through the eye is interrupted or impaired, a change in the intra-ocular pressure of the eye will result. It is, therefore, quite important to be able to readily, accurately and safely measure intra-ocular pressure in order to diagnose glaucoma and the like.

However, because the eye is an enclosed member, it is not practical to measure the intra-ocular pressure in a living eye directly. Accordingly there has been developed a variety of instruments for measuring the pressure indirectly. The instruments used for this purpose are known as tonometers.

In general, most tonometers in use today work on either of two principles. The first involves applying a known force to the cornea of an eye and measuring the deformation produced. The instruments using this principle are known as "impression or indentation" tonometers. The second involves applying a standard or known deformation to the eye and measuring the force required to produce the deformation. The instruments using the second principle are called applanation tonometers. The two principal types are distinguished in that in the first case, the cornea is indented and in the second case, the cornea is merely flattened. The present invention utilizes the second principle.

Because the eye is a relatively sensitive organ, it is difficult for one whose eye is being examined to restrain from flinching or blinking when the cornea is touched. For this reason, the use of many prior known tonometers requires that the eye be anesthetized. Since anesthetizing an eye is considered a serious medical procedure, trained personnel are frequently required to carry it out. Even when trained personnel are available, the anesthetizing of an eye is to be avoided if at all possible because of the possibility of an inadvertent injury to the eye as might be caused by rubbing or striking the cornea with a sharp object which goes unnoticed because of the anesthetic. If the use of an anesthetic can be avoided, not only will the possibility of an inadvertent injury going unnoticed be reduced, but intra-ocular pressure measurements could be taken by a wider group of personnel at lower cost and with the attendant advantage that more people would undoubtedly be able to afford an earlier diagnosis of a serious abnormal eye condition.

In addition to the problems associated with having to anesthetize an eye when using many of the prior known tonometers, there has been also a problem in interpreting the results of the measurements taken. The results of the measurements taken with many prior known tonometers are recorded on paper by a pen-recorder. The wave forms recorded are irregular and vary from patient to patient. This is due in part to the fact that the volume of the eye is invariably changed during a measurement. Because of this, it is the practice to make allowances for the pressure change due to the change in eye volume and to also allow for the effects of the various mechanical forces involved in the bending of the corneal surface. These factors tend to result in inaccurate measurements and require a good deal of guessing, which is especially difficult using pen-recorded pressures, as to what the actual equivalent pressure is in an undisturbed eye.

In addition to the desirability of providing a tonometer apparatus which does not require the anesthetizing of an eye and which provides a more accurate readout of intra-ocular pressure without the necessity for relying on the educated interpretations of pen-recorded pressures, there is also a need for a reliable and accurate means for measuring the internal pressure of other types of enclosed members. For example, a considerable need exists for an apparatus for reliably, accurately and automatically measuring tire pressure on large trucks, aircraft and other vehicles.

Presently, conventional means for accurately measuring tire pressure involves the use of a gauge applied to the valve stem of the tire. This results in a direct measurement of pressure. For vehicles carrying a number of tires, this procedure is time-consuming and, therefore, costly.

There is also believed to be a considerable need for analyzing the condition of fruits and vegetables in a more automatic and economical fashion. Since the condition of the skin of fruits and vegetables is often closely related to the condition of the produce itself, it is believed that an accurate measurement of the mechanical characteristics of the skin as well as the internal pressures in the produce can quickly determine the condition of the produce.

SUMMARY OF THE INVENTION

In view of the foregoing, a principal object of the present invention in general is a novel apparatus and method for measuring internal pressure indirectly, and in particular an apparatus and method for providing a readout of intraocular pressure, which does not require the administration of an anesthetic in its use.

In a preferred embodiment, the apparatus includes a novel transducer. The transducer is provided with a predetermined surface area comprising a fixed surface surrounding or at least extending for a predetermined distance on opposite sides of a spring-biased movable piston. Coupled to the piston is a variable capacitor. The capacitance of the capacitor varies in proportion to the distance the piston is moved relative to the surrounding or adjacent surface areas for providing an output proportional to the force required to move the piston. Since the area of the piston and surrounding surface is known, the force required to move the piston is equatable to pressure.

Coupled to the output of the transducer is a means responsive to changes in the transducer output for providing a digital readout of the pressure applied to the transducer when a change in the slope of the output of the transducer has a predetermined polarity and exceeds a predetermined rate.

In the preferred embodiment of the invention, the means described for providing the digital readout comprises a first means for providing a first signal proportional to the first derivative of the output and a second means for providing a second signal proportional to the second derivative of the output. Coupled to the first and second signal-providing means is an analog-to-digital converter. Coupled to the converter are four registers and an equal number of associated digital display circuits for displaying the contents of the registers each time a measurement is made.

Another object of the invention is a pressure-measuring apparatus and method of the type described above with a transducer adapted to measure the internal pressure of different enclosed members as well as selected physical characteristics of the external walls of such members

DESCRIPTION OF THE DRAWINGS

The above and other objects, features and advantages of the present invention will become apparent from a reading of the following detailed description of the accompanying drawings in which.

DETAILED DESCRIPTION

Figure 1:
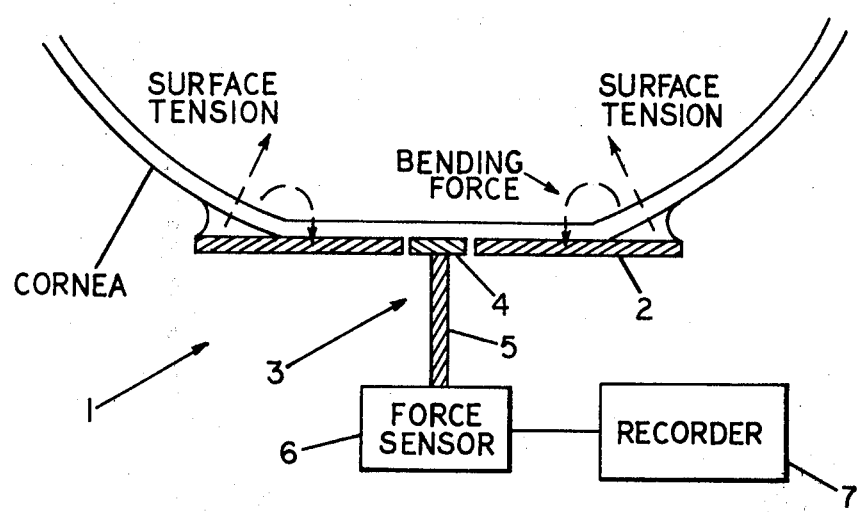
FIG. 1 is a diagrammatic representation of an applanating transducer in contact with the cornea of an eye.

Referring to FIG. 1, there is shown in a horizontal cross-section a diagrammatic representation of a prior known applanating transducer 1 in contact with the cornea of the eye. The transducer 1 is provided with an annular foot-plate or guard-ring 2. In the center of the foot-plate 2 is a movable spring-biased piston or plunger 3 comprising a circular head member 4 and a connecting rod 5. The rod 5 is coupled to a force sensitive device 6 which, by means of a change in mutual inductance of movable coils, provides an output proportional to the distance the piston head 4 moves relative to the foot-plate 2. The output of the device 6 is recorded as by a pen-recorder 7.

In practice, the range of movement of the piston head 4 relative to the foot-plate 2 is extremely small (of the order of a few microns) so that the surfaces of the piston head and foot-plate are always virtually in the same plane. When the piston head and foot-plate, the surfaces of which comprise an applanating surface because they flatten the cornea, is pressed against the cornea, the force exerted on the piston is the product of the pressure in the eye and the area of the piston head. The electrical output of the device 6, which is proportional to the changes in the force exerted on the piston as the transducer is pressed gently against the cornea, provides a wave form, a typical example of which is shown in FIG. 2.

Figure 2:
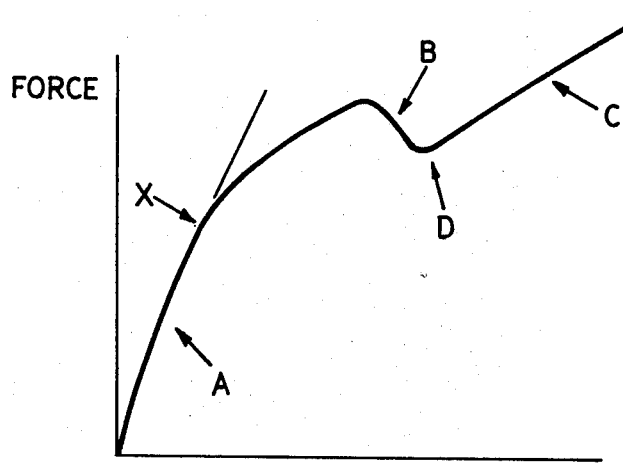
FIG. 2 is a diagram of a simplified representative tonograph obtained using prior known tonometer apparatus.

Referring to FIG. 2, the force on the plunger increases as shown at A until the whole surface of the piston head is in contact with the cornea; then, as the area of corneal contact spreads onto the surrounding foot-plate, the force on the piston remains constant or decreases slightly as shown at B. The decrease at B is thought to be due to some little understood relaxation of the eye surfaces or interaction between the eye and the transducer. Finally, as the transducer is pressed still more firmly against the eye, the force on the piston increases again as shown at C. The latter increase is considered to be due principally to forces resulting from a forced change in the volume of the eye, bending forces, surface tension and the like.

Since tonometry involves the application of a force to the eye, it is inevitably accompanied by a rise of intra-ocular pressure, usually termed $P_t$. The pressure which is of clinical interest, however, is the pressure, $P_o$, which exists in the undisturbed eye before the tonometer is applied. It is generally accepted that the theory of applanation tonometry is based on the principle that, if an object having a flat surface is pressed with a force W against a spherical container bounded by a flexible membrane and having an internal pressure, $P_t$ the equilibrium condition is given by $$W = P_t A$$

That is, the applanating force is balanced by the product of the internal pressure and the area over which the latter acts. This equation expresses the so-called Imbert-Fick law, but this simple relationship is strictly valid only for a spherical container, the limiting membrane of which is infinitely thin, perfectly flexible and elastic, and dry. The cornea fulfills none of these requirements. Since the cornea of the human eye is about 0.5 mm thick, the area flattened on its external surface differs from that on its internal surface, and, because the corneal tissue is not perfectly flexible, a small proportion of the deforming force is expended in bending the cornea around the circumference of the applanated area. Moreover, since the cornea is wet, the surface tension of the tear film tends to pull the applanating surface onto the cornea. The conditions prevailing during applanation tonometry are therefore more realistically represented by the equation $$W + s = P_t A_i + b$$

where $s$ is the extra force due to surface tension tending to pull the applanating surface against the cornea, $b$ is the force required to bend the cornea, and $A_i$ is the area of flattening of the inner cornea surface against which the elevated intra-ocular pressure, $P_t$, acts.

Because of the various factors described above, many of which are not readily determinable, but which enter into a measurement of intra-ocular pressure, it has been the practice to accept as a close approximation of the actual intra-ocular pressure, $P_o$, in an undisturbed eye, the lowest pressure obtained from this type of tonometer. Typically, the lowest pressure obtained has been the pressure immediately preceding the second rise C in pressure, as shown in FIG. 2 at D.

In contrast to the tonometer described above, commonly known as a Mackay-Marg, a tonometer known as the Goldmann has been considered as probably the most accurate of the instruments used in that illumination of the cornea with a slit-lamp and the use of a microscope have typically provided lower pressure readings more closely approximating the intra-ocular pressure in an undisturbed eye. The Goldmann is, however, a complex instrument requiring skilled operators.

In the course of attempting to improve the accuracy of the Mackay-Marg tonometer, while retaining the advantageous features of that tonometer, it was discovered that there exists a point of significant pressure inflection during the initial rise in pressure, as at the point $x$ in FIG. 2, and that the magnitude of the pressure at that point corresponds significantly with intraocular pressure readings obtained with a Goldmann. It was also found that the change in the slope of the pressure has a characteristic polarity and a significant rate of change. The readings thus obtained with the present invention are considered to be particularly significant since the results are obtained without the need for anesthetizing the eye and can be read directly without the need for interpolating and estimating the results from a graph of the pressures as heretofore has been required.

Figure 3:
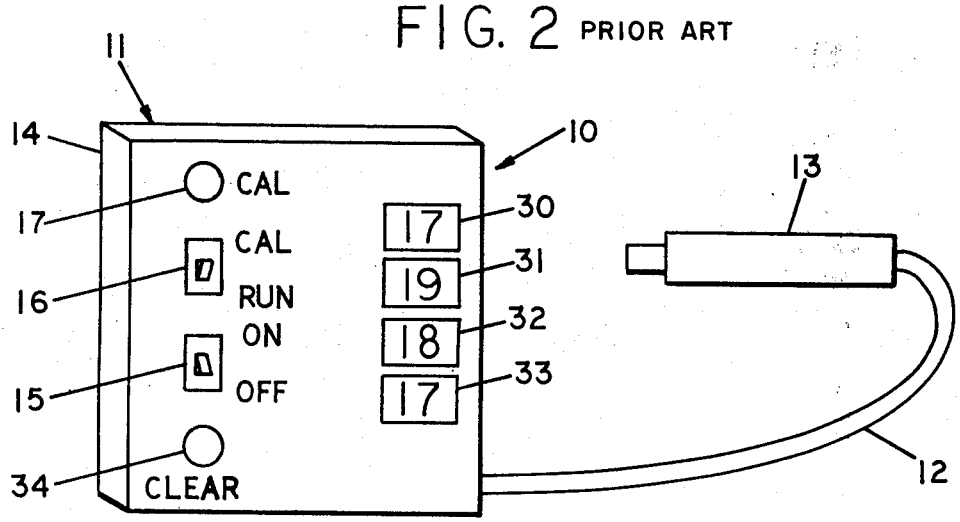
FIG. 3 is a perspective view of a pressure-measuring apparatus according to the present invention.

Referring to FIG. 3, there is provided, in view of the foregoing and in accordance with the present invention, an applanation tonometer 10 comprising an electronic assembly 11 to which is coupled, by means of a cable 12, a transducer 13.

Assembly 11 is provided with a housing 14 having a front face in which is provided an on/off switch 15, a calibrate/run switch 16, a rotatable calibration control 17, a plurality of digital readouts, 30, 31, 32 and 33, and a clear button or switch 34.

Figure 4:
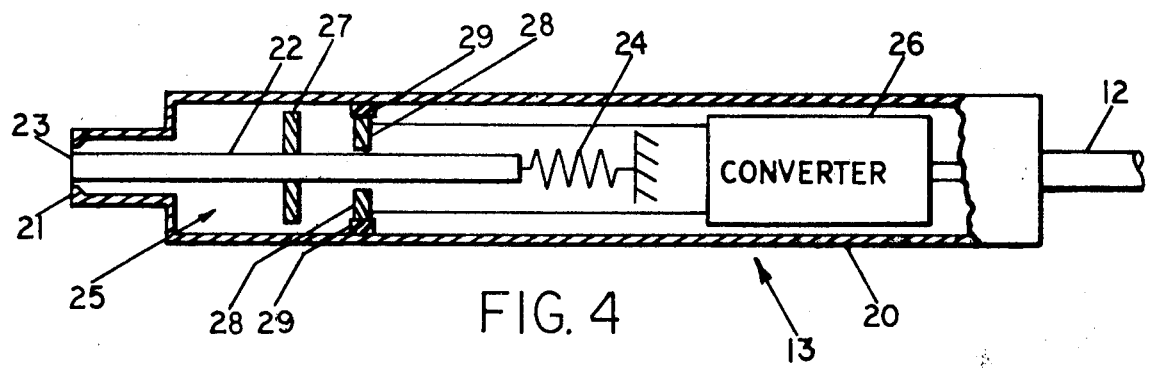
FIG. 4 is a partially broken away side view of a transducer according to the present invention.
Figure 5:
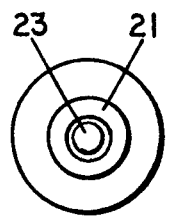
FIG. 5 is an end view of FIG. 4.

As shown in more detail in FIGS. 4 and 5, transducer 13 is provided with a pencil-shaped housing 20. Housing 20 has a diameter and a length designed for permitting the transducer to be hand-held, and is provided at one end with an annular flat applanating surface 21 having an outside diameter suitable for applanating the cornea of an eye. In the interior of housing 20 is a movable plunger 22. Plunger 22 is essentially an elongated rod or shaft having at one end a planar surface 23. Surface 23 is essentially in the plane of the surface 21 but is movable with respect thereto a small distance, as of a few microns. Plunger 22 is spring biased as by a spring 24 and is coupled to a variable capacitor 25, which constitutes a part of a capacitance-to-voltage converter 26. Capacitor 25 comprises at least one annular plate 17, fixed to the plunger, which moves with a movement of the plunger and one or more plates which are fixed to the housing 20 as by insulators 29, such that the capacitance of the capacitor 25 varies in proportion to the movement of the plunger. As will be apparent, converter 26, and hence transducer 13, output a signal which is dependent on the capacitance of capacitor 25 and consequently is proportional to the movement of the plunger.

Figure 6:
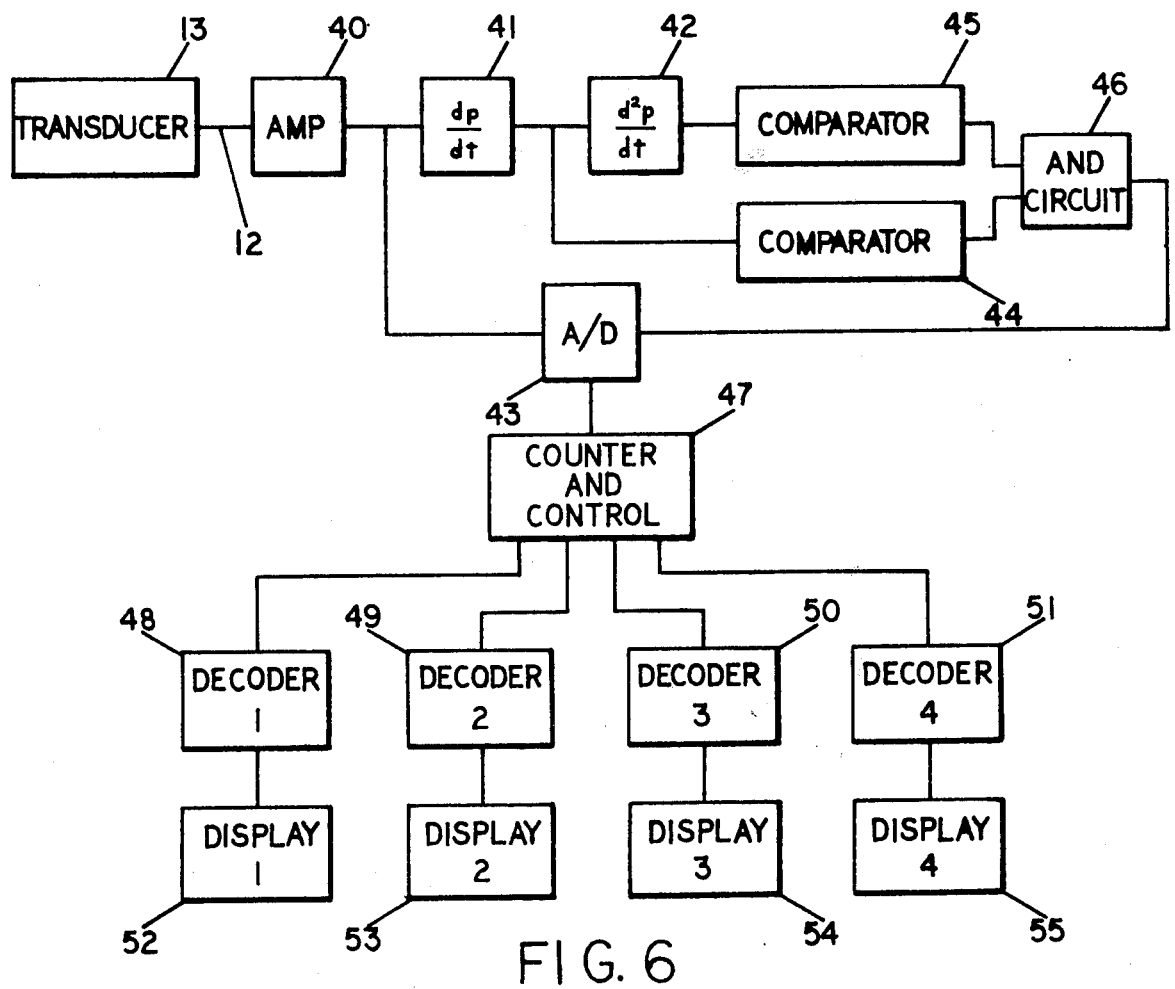
FIG. 6 is a block diagram of the apparatus of FIG. 3.

Referring to FIG. 6, transducer 13 is coupled, by means of an amplifier 40, to a pair of series-coupled differentiating circuits 41 and 42 and to an analog-to-digital converter 43. Circuits 41 and 42 are also coupled, respectively, by means of a pair of comparator circuits 44 and 45, in series with a dual-input AND and flip-flop circuit 46 to the analog-to-digital converter 43. Converter 43 is, in turn, coupled, by means of a counter-and-control circuit 47 to a plurality of decoder driver/latch circuits 48, 49, 50 and 51 which, respectively, are provided to drive an equal number of display circuits 52, 53, 54 and 55 corresponding, respectively, to the digital readouts 30, 31, 32 and 33 of FIG. 3. Counter-and-control circuit 47 comprises means for switching the output of the converter 43 to a different one of the decoder driver/latch circuits 48-51 after each reading in any suitable manner.

In a preferred embodiment of the present invention, the circuit components described with respect to FIG. 6 individually comprise integrated circuits and seven segment digital displays which are commercially available as follows:

| Component | Device Type | Source |
|---|---|---|
| converter 26 | 7413 | Fairchild |
| amplifiers 40 | 1458 | Motorola |
| differentiators 41 and 42 | 1458 | '' |
| comparators 44 and 45 | 3302 | '' |
| A/D converter 43 | 1458 | '' |
| | 555 | Signetics |
| AND/Flip-Flop 46 | 7400 | Motorola |
| counter-and-control 47 | 93L10 | Fairchild |
| | 93L00 | '' |
| decoder driver/latches | 9368 | '' |
| displays 52–55 | FND70 | '' |

Obviously, components other than those suggested in the above list may also be used in a particular application in lieu of those listed.

In practice, an operator holds the transducer 13 in substantially the same manner as a person holds a pencil and gently taps the cornea of an eye being examined. As the transducer contacts the cornea, the plunger 22 is moved changing the capacitance of the capacitor 25, which results in a variable d.c. output signal from the transducer, having a magnitude proportional to the movement of the plunger and hence proportional to pressure. The output of the transducer 13 is amplified by amplifying circuit 40 and applied to the analog-to-digital converter 43 and to the input of the differentiating circuit 41. The output of circuit 41, which is proportional to the first derivative of the output of the transducer 13, is compared with a reference potential, such as ground potential, in the comparator circuit 44. If the output of circuit 41 is positive, a signal is applied by circuit 44 to one input of the AND circuit 46 for indicating that a change in the slope of the pressure being measured by the transducer has a predetermined polarity - namely, positive.

The output of circuit 41 is also differentiated by circuit 42 for providing an output proportional to the second derivative of the output of the transducer 13. The latter output is also compared with a predetermined reference potential in the comparator 45. If the rate of change of the slope of the pressure measured by the transducer 13 exceeds a predetermined magnitude, the output of circuit 42 will exceed the reference potential in the comparator 45 and comparator 45 will output a signal which is applied to the second input of the AND circuit 46. When the outputs of circuits 44 and 45 coincide in AND circuit 46, there is a change in the slope of the pressure being measured by the transducer 13 which is both positive and exceeds a predetermined rate, and AND circuit 46 generates a trigger signal for triggering converter 43.

When converter 43 is triggered by the signal from AND circuit 46, the digital equivalent of the pressure then being measured by transducer 13 is routed, by control circuit 47, in a conventional manner from converter 43 to one of the decoder driver/latch circuits 48-51 for display in an associated one of the displays 52-55. In a typical sequence, control circuit 47 routes the first reading to display 52, the next to display 53, and so on, such that an operator is thereby able to choose the lowest of the readings as that most nearly approximating the intra-ocular pressure in an undisturbed eye.

Since the digital readouts of pressure are provided only when the change in the slope of the output of the transducer has a predetermined polarity and exceeds a predetermined rate, the use of multiple readouts further insures a correct application of the transducer to the cornea. Thus, if one or more of the readouts is widely divergent from another of the readouts, the operator might well clear the instrument using the clear button 34 and retake the readings. The calibrate switch 17 is used simply to calibrate the instrument initially before any readings are taken as is conventional with most measuring instruments.

It is important to note that, because of the high frequency response of the apparatus of the present invention, readings of pressure can be made quickly and with very little force exerted on the cornea and that, for this reason, the apparatus can be used safely and reliably without anesthetizing the eye.

In addition to the above described preferred embodiment in which both the polarity and the rate of change of the slope of the output of the transducer 13 is detected and used for providing a digital output of the intra-ocular pressure, it is also understood that in a less sophisticated embodiment, the detection and use of the polarity of a change in the slope may be omitted. In such an embodiment, accurate intra-ocular pressures will still be obtainable in most cases since the detection of the polarity of a change in the slope of the output is principally related to the detection of the negative going portion B of the curve of FIG. 2. As is apparent from the description of the preferred embodiment above, this area of the curve is seldom reached before a readout is obtained.

Another modification which may be made to either or both of the above described embodiments without departing from the spirit and scope of the present invention is the elimination of the analog-to-digital converter and related circuitry. In this case, means are provided responsive to the output of the AND circuit 46 for recording directly the analog output of the amplifier 40. Such means, for example, may include a digital voltmeter or the like for indicating the intra-ocular pressure at the time of the output from circuit 46.

While at least two embodiments of the present invention are described as having particular utility in connection with the measurement of intra-ocular pressure, it is contemplated that the apparatus of the present invention also has utility in connection with the measuring of the internal pressure of other enclosed members, such as a tire. When used in this application, the transducer 13 would be fabricated with larger and stronger applanating surfaces, but the principles of operation would remain the same.

As a further modification, when used as a device for measuring tire pressure, for example, the transducer foot-plate surfaces 21 might well comprise a pair of spaced parallel fixed surfaces. The plunger 22 in that arrangement would then have a rectangular-shaped head surface lying essentially in the plane and intermediate the parallel fixed surfaces in order that the movement of the plunger would correspond to internal tire pressure as the tire is rolled over the plunger.

These and other modifications will undoubtedly occur to those familiar with the present invention and, therefore, it is understood that the description of the preferred embodiment provided herein is only for purposes of illustration and that the scope of the invention is to be determined from the claims hereinafter provided.

What is claimed is:
1. A pressure measuring apparatus comprising:
    means responsive to a variable pressure for providing an output signal proportional to said pressure; and
    means responsive to a predetermined change in said output signal for indicating the magnitude of said pressure at the time of said predetermined change, said indicating means comprising:
    means responsive to said output signal for outputting a first and a second signal proportional, respectively, to the first and second derivatives of said output signal;
    means responsive to said first and said second signals for providing a digital output corresponding to the output of said pressure-responsive means when said first derivative has a predetermined polarity and said second derivative exceeds a predetermined magnitude;
    means for storing said digital output; and
    means coupled to said storing means for visually displaying the magnitude of said digital output.

2. An apparatus according to claim 1 wherein said means for providing said digital output comprises an analog-to-digital converter.

3. An apparatus according to claim 1 wherein said storing means comprises a plurality of digital registers and said displaying means comprises separate displaying means coupled to each of said digital registers for displaying the contents of each of said digital registers and further comprising means for storing separate digital outputs corresponding to the output of said pressure-responsive means in each of said plurality of digital registers for each of an equivalent number of time in a given sequence that said first derivative has a predetermined polarity and said second derivative exceeds a predetermined magnitude.

4. A method of measuring the internal pressure of an enclosed member having a flexible wall comprising the steps of:
    causing a movable piston disposed between fixed surfaces to bear against said wall;
    generating a signal proportional to the distance said piston moves relative to said fixed surfaces;
    detecting a change in the slope of said signal as said piston and surfaces are brought to bear against said wall; and
    automatically measuring the magnitude of said signal when said change in the slope of said signal exceeds a predetermined rate, said steps of detecting a change in the slope of said signal and measuring the magnitude of said signal comprising the steps of:
    differentiating said signal for generating a first and a second differential signal;
    comparing said first and said second differential signal with a first and a second reference signal, respectively; and
    generating a control signal for controlling an analog-to-digital conversion circuit to provide said measurement of the magnitude of said signal when there is a predetermined relationship between said first and said second differential signal and said first and said second reference signal, respectively.

5. A method according to claim 4 wherein said step of measuring the magnitude of said signal further comprises the step of automatically routing the output of said analog-to-digital display circuits to simultaneously display the results of a corresponding number of pressure measurements.

6. A method according to claim 4 wherein said step of generating a signal proportional to the distance said piston moves relative to said fixed surfaces comprises the step of changing the capacitance of a variable capacitor in proportion to the distance said piston moves relative to said fixed surfaces.

* * * * *